(12) United States Patent
Tanaka

(10) Patent No.: US 9,188,238 B2
(45) Date of Patent: Nov. 17, 2015

(54) FLOW CHANNEL SWITCHING VALVE

(71) Applicant: SHIMADZU CORPORATION, Kyoto-shi, Kyoto (JP)

(72) Inventor: Shinji Tanaka, Osaka (JP)

(73) Assignee: SHIMADZU CORPORATION, Kyoto (JP)

( * ) Notice: Subject to any disclaimer, the term of this patent is extended or adjusted under 35 U.S.C. 154(b) by 77 days.

(21) Appl. No.: 14/196,062

(22) Filed: Mar. 4, 2014

(65) Prior Publication Data
US 2014/0261814 A1 Sep. 18, 2014

(30) Foreign Application Priority Data

Mar. 15, 2013 (JP) .................................. 2013-052969

(51) Int. Cl.
*F16K 11/074* (2006.01)
*F16K 31/04* (2006.01)
*G01N 30/20* (2006.01)

(52) U.S. Cl.
CPC ............. *F16K 31/042* (2013.01); *F16K 11/074* (2013.01); *G01N 2030/202* (2013.01); *Y10T 137/86863* (2015.04)

(58) Field of Classification Search
CPC ..................... Y10T 137/86863; F16K 11/074; F16K 11/0743
See application file for complete search history.

(56) References Cited

U.S. PATENT DOCUMENTS

| | | | | |
|---|---|---|---|---|
| 3,297,053 A | * | 1/1967 | McKinney | 137/625.46 |
| 3,868,970 A | * | 3/1975 | Ayers et al. | 137/625.46 |
| 4,705,627 A | * | 11/1987 | Miwa et al. | 210/264 |
| 5,207,109 A | * | 5/1993 | Olsen | 73/863.73 |
| 6,390,127 B2 | * | 5/2002 | Schick | 137/625.11 |
| 6,910,503 B2 | * | 6/2005 | Schick et al. | 137/625.47 |
| 7,195,229 B2 | * | 3/2007 | Maeda | 251/205 |
| 8,876,081 B2 | * | 11/2014 | Tower | 251/208 |

FOREIGN PATENT DOCUMENTS

JP 2008-215494 A 9/2008

* cited by examiner

*Primary Examiner* — John Fox
(74) *Attorney, Agent, or Firm* — Westerman, Hattori, Daniels & Adrian, LLP

(57) ABSTRACT

A flow channel switching valve is provided in which a stator and a rotor are contained in an internal space of a housing, and a packing is sandwiched between a flow channel connection plane, which is one plane of the internal space of the housing, and the stator. In the flow channel connection plane of the housing, a packing gland is provided at a distance from a flow channel connection portion so as to surround an outer circumference of the flow channel connection portion, and the packing gland is in contact with a circumferential edge portion of the packing on the same plane as the flow channel connection portion.

4 Claims, 2 Drawing Sheets

FLOW CHANNEL SWITCHING VALVE

BACKGROUND OF THE INVENTION

1. Field of the Invention

The present invention relates to a flow channel switching valve for use in, for example, an auto-sampler that introduces a sample to an analysis flow channel of a liquid chromatograph.

2. Description of the Related Art

As an example, in an auto-sampler that introduces a sample to an analysis flow channel of a liquid chromatograph, after the sample is taken into a sample loop from a sample container, the sample loop is connected to an upstream side of a separation column in the analysis flow channel by switching of a flow channel switching valve, which allows the sample in the sample loop to be transported to a separation column side by a mobile phase flowing in the analysis flow channel.

As the flow channel switching valve for use in the liquid chromatograph, a rotary type switching valve is common. The rotary type switching valve switches a connected flow channel by rotating a rotor (rotary part) (e.g., refer to Unexamined Japanese Patent Publication No. 2008-215494).

In the rotary type switching valve, a plurality of connection ports for connecting flow channel piping are provided in an upper portion of a housing, and a rotor and a stator (stationary part) are contained inside the housing. The rotor and the stator are in contact with each other in a state where planes thereof keep liquid tightness with each other, and the stator is fixed by a pin or the like so as not to rotate with respect to a housing side. Through-holes are provided at positions of the stator corresponding to holes of end portions of flow channels leading to the connection ports of the housing. In a surface on a stator side of the rotor, a groove communicating between end portions of the through-holes of the stator is cut, and the rotor is driven and rotated while sliding on the stator to thereby change a position of the groove and switch the connection between the connection ports.

There is also a flow channel switching valve in which the stator is integrated with the housing. It has been known that when the flow channel switching valve is used under a condition of high-pressure liquid feed, the flow channel switching valve in which the stator is integrated with the housing is higher in durability than the flow channel switching valve in which the stator and the housing are configured as separate bodies.

As a cause for decreasing the durability of the flow channel switching valve in which the stator and the housing are provided as separate bodies, in the flow channel switching valve in which the stator is provided as the separate body from the housing, a packing made of a resin is sandwiched between the stator and the housing in order to keep liquid tightness between the stator and the housing, and it is considered that this packing is inclined by influence of a liquid feed pressure.

Normally, in order to increase a contact pressure at a flow channel connecting section between the housing and the packing, a periphery of a region where the end portions of the flow channels leading to the connection ports on the housing side is depressed, and a central portion of a plane of the packing and the region where the end portions of the flow channels on the housing side come into intensive contact with each other, thereby increasing the contact pressure, and a circumferential edge portion of the packing is not in contact with an inner wall surface of the housing. Thus, if a bias occurs in the contact pressure acting on a surface of the packing from the stator side, the packing may be inclined. If the packing is inclined, a bias occurs in a contact pressure acting on a contact surface of the stator with the rotor, and a portion on which the high contact pressure acts is locally worn away.

Liquid flowing between the two connection ports connected by the groove of the rotor is guided to the groove of the rotor through the through-holes provided in the packing and the stator from the connection port on an entrance side, and is further guided from the groove of the rotor to the connection port on an exit side through the through-holes of the stator and the packing leading to the connection port on the exit side. Since an inner diameter of the through-holes provided in the stator and the packing is smaller than a width of the groove provided in the rotor, a high liquid pressure acts on the stator side from a rotor side at a portion where the liquid flows from the groove of the rotor to the through-hole of the stator. If this portion on which the high liquid pressure acts deviates from a central portion of the stator, a force that tries to incline the stator exerts, which causes a bias in the contact pressure acting on the packing from the stator, so that the packing is inclined.

SUMMARY OF THE INVENTION

An object of the present invention is to suppress inclination of a packing sandwiched between a stator and a housing and enhance durability of a flow channel switching valve.

In a flow channel switching valve according to the present invention, a stator and a rotor are contained in an internal space of a housing, and a packing is sandwiched between a flow channel connection plane and the stator, the flow channel connection plane being one plane of the internal space of the housing. Furthermore, in the flow channel connection plane of the housing, a packing gland is provided at a distance from a flow channel connection portion so as to surround an outer circumference of the flow channel connection portion, and the packing gland is in contact with a circumferential edge portion of the packing on the same plane as the flow channel connection portion.

The housing has a plurality of connection ports connecting flow channel piping, and an internal space, and is provided with the flow channel connection portion as a plane projected from a periphery thereof, the flow channel connection portion being a region where holes of end portions of flow channels respectively leading to the connection ports are arranged in the flow channel connection plane, which is the one plane of the internal space.

The stator is contained inside the housing, is made of a flat plate-like member having a plane larger than the flow channel connection portion, and is fixed to a flow channel connection plane side of the housing with the packing interposed.

The packing is made of a flat plate-like member having a plane larger than the flow channel connection portion, and is sandwiched between the flow channel connection plane of the housing and the stator so that a central portion of one plane thereof tightly adheres to the flow channel connection portion.

The rotor has a plane in contact with a plane of the stator on an opposing side of the packing inside the internal space of the housing, and is formed with a groove communicating between any one pair of the connection ports in the plane. The rotor is provided with a rotor drive portion that rotates the rotor while sliding the rotor on the stator.

Furthermore, the packing gland is provided at a distance from the flow channel connection portion so as to surround an outer circumference of the flow channel connection portion in the flow channel connection plane of the housing, and the packing gland is in contact with a circumferential edge portion of the packing on a same plane as the flow channel connection portion. "The packing gland is in contact with the circumferential edge portion of the packing on the same plane as the flow channel connection portion" means that the packing gland is in contact with the circumferential edge portion of a surface of the packing on the side in contact with the flow channel connection portion.

Since the flow channel switching valve of the present invention includes the packing gland that is provided at a distance from the flow channel connection portion so as to surround the outer circumference of the flow channel connection portion in the flow channel connection plane of the housing, and is contact with the circumferential edge portion of the packing on the same plane as the flow channel connection portion, inclination of the packing can be suppressed under a condition of high-pressure liquid feed, and the occurrence of a bias in contact pressure applied to the contact surface between the stator and the rotor can be suppressed. This can prevent the stator from being locally worn away, and can enhance durability of the flow channel switching valve under the condition of high-pressure liquid feed.

DETAILED DESCRIPTION OF THE INVENTION

As to a packing gland in a flow channel switching valve of the present invention, it is preferable that a member made of a material having a smaller modulus of elasticity than that of a packing is caused to tightly adhere to an inner wall of a housing. It is considered that when the packing gland is provided, a contact pressure received by a flow channel connection portion of the housing from the packing is also distributed to the packing gland, thereby deteriorating liquid tightness in a flow channel connection section between the housing and the packing. Consequently, the packing gland is made of material having the smaller modulus of elasticity than that of the packing, which can make smaller a contact pressure received by the packing gland from the packing than the contact pressure received by the flow channel connection portion of the housing from the packing, and can suppress the deterioration in liquid tightness in the flow channel connection section between the housing and the packing.

As the above-described preferred aspect, an example is cited in which if the packing is made of polyether ether ketone or polyimide, the packing gland made of polytetrafluoroethylene is used.

Moreover, the packing gland may be made of the same material as that of the housing, and may be formed integrally as a part of the inner wall of the housing. Since when the packing gland is configured by the same material as that of the housing, the contact pressure equivalent to the contact pressure applied to the flow channel connection portion of the housing is applied to the packing gland as well, the liquid tightness in the flow channel connection section between the housing and the packing is deteriorated. However, by forming the packing gland so as to make a contact area between the packing gland and the packing small, the deterioration in the liquid tightness in the flow channel connection section between the housing and the packing can be suppressed.

Figure 1:
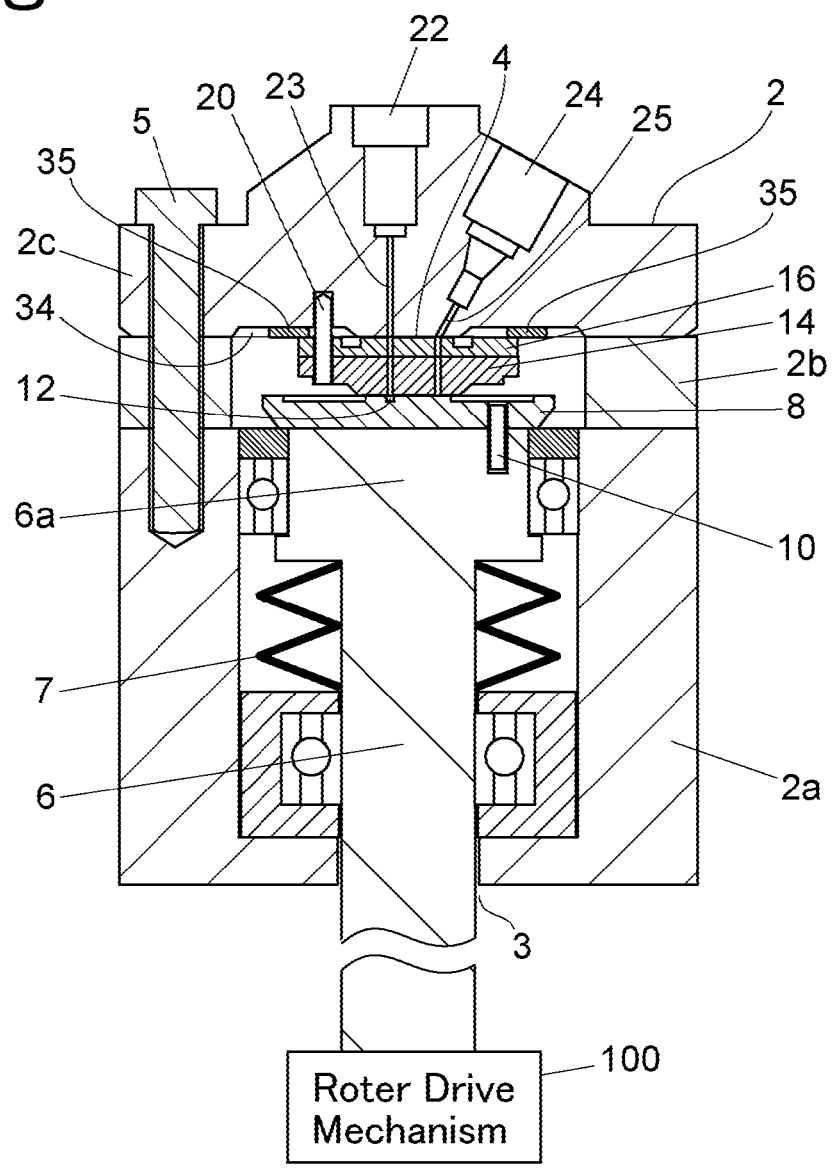
FIG. 1 is a cross-sectional view showing one embodiment of a flow channel switching valve.

One embodiment of a flow channel switching valve will be described with reference to FIG. 1.

In an internal space of a housing 2, a rotor 8 as a rotary part, and a stator 14 as a stationary part are contained. The housing 2 is circular in a planar shape, and includes a plurality of connection ports 22, 24 connecting flow channel piping in an upper outer surface. In a central portion of a lower surface of the housing 2, a hole 3 is provided, and a rotor drive shaft 6 that rotates the rotor 8 penetrates the hole 3. The rotor drive shaft 6 is supported rotatably by a bearing inside the housing 2, and is coupled to a rotor drive mechanism 100 that rotates the rotor drive shaft 6 outside the housing 2. The rotor drive shaft 6 and the rotor drive mechanism 100 make up a rotor drive portion.

The housing 2 is made up of three members of a housing body 2a, an intermediate member 2b, and a housing top 2c. The housing body 2a has a cylindrical shape, and the hole 3 is opened at a center of a seating surface. In a state where an opening of the housing body 2a is in an upward direction, the ring-shaped intermediate member 2b is placed on the opening, and the disc-shaped housing top 2c is placed on the intermediate member 2b. The housing body 2a serves as a base for the housing 2, and the intermediate member 2b and the housing top 2c are detachably attached to the housing body 2a by bolts 5. The bolts 5 are fastened so as to penetrate the intermediate member 2b from an upper surface side of the housing top 2c located in an upmost portion of the housing 2 and reach the housing body 2a. The housing top 2c is provided with through-holes through which the bolts 5 penetrate the housing top 2c, and the intermediate member 2b is also provided with through-holes through which the bolts 5 penetrate the intermediate member 2b. The housing body 2a is provided with screw holes to fasten the bolts 5. Although in FIG. 1, only one attachment position of the bolts 5 is illustrated, the bolts 5 are attached at three even positions in a circumferential edge portion on a plane viewed from an upper surface side of an upper surface of the housing top 2c. The attachment positions of the bolts 5 are not limited thereto.

In a lower surface (a flow channel connection plane) of the housing top 2c, which is an internal wall surface of the housing 2, a flow channel connection portion 4 is provided. The flow channel connection portion 4 is a plane where holes of end portions of flow channels 23, 25 leading to the connection ports 22, 24 are arrayed. The flow channel connection portion 4 is a circular plane region with a periphery surrounded by a ring-shaped depression 34. The stator 14 is in contact with the flow channel connection portion 4 with a packing 16 interposed. The stator 14 and the packing 16 are each a circular member larger than the flow channel connection portion 4 in a planar shape, and a central portion of the packing 16 is in contact with the flow channel connection portion 4 while keeping liquid tightness. The provision of the depression 34 in a periphery of the flow channel connection portion 4 allows a portion of the housing top 2c in contact with the packing 16 to be limited to the flow channel connection portion 4, thereby increasing a contact pressure between the flow channel connection portion 4 and the central portion of the packing 16, and enhancing the liquid tightness in this portion.

A packing gland 35 is provided on a housing top 2c side. The packing gland 35 is caused to tightly adhere to a bottom portion of the depression 34 in contact with a circumferential edge portion of the packing 16 on the same plane as the flow channel connection portion 4. The packing gland 35 is a ring-shaped member made of a material having a smaller modulus of elasticity than that of the packing 16. As the material of the packing gland 35, for example, in the case where the material of the packing 16 is a resin such as polyether ether ketone and polyimide, polytetrafluoroethylene can be used. The packing gland 35 is in contact with the circumferential edge portion of the packing 16 on the same plane as the flow channel connection portion 4, by which the packing 16 can maintain a posture without being inclined, even if a biased contact pressure is applied to the packing 16 from a stator 14 side by influence of high-pressure liquid feed.

While in this embodiment, the packing gland 35 is a ring-shaped member, the packing gland 35 may be made up of a plurality of members arranged along a circumferential surface of the packing 16. In short, any structure that can support the circumferential edge portion of the packing 16 on the housing top 2c side to thereby prevent the inclination of the packing 16 can be employed.

Figure 2:
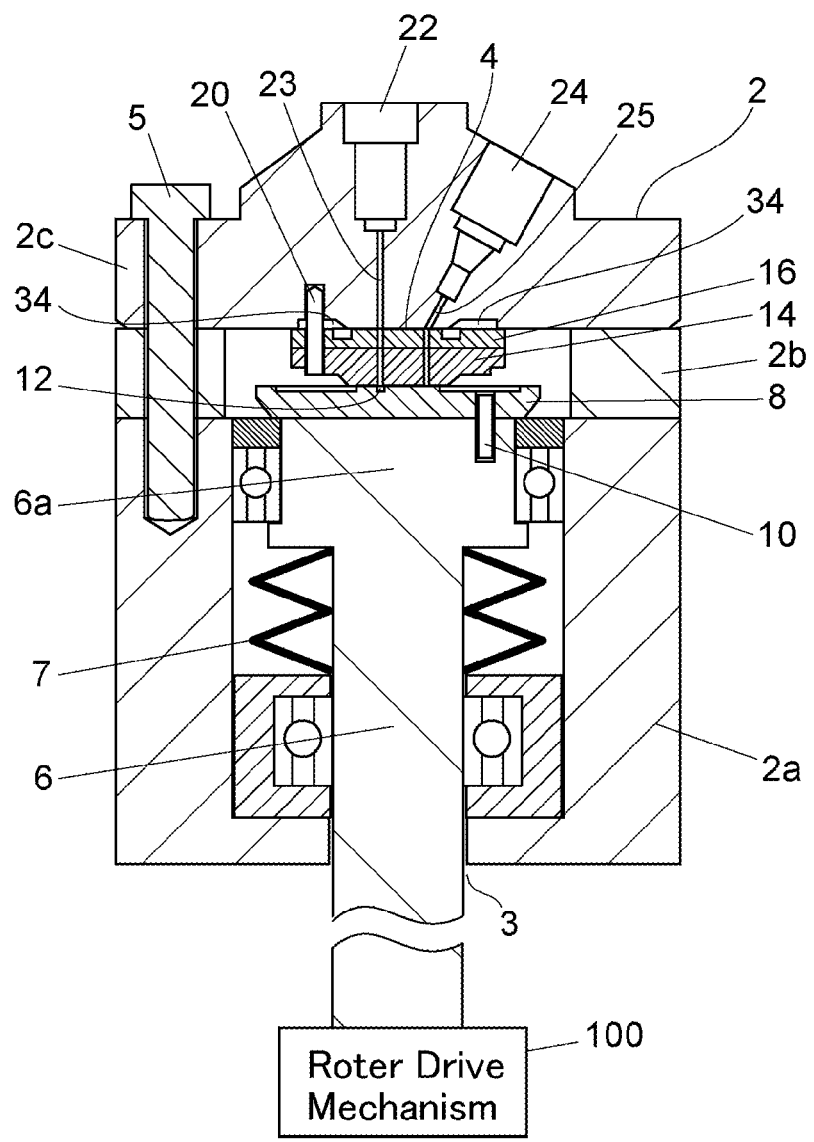
FIG. 2 is a cross-sectional view showing another embodiment of the flow channel switching valve.

As shown in FIG. 2, a shape of the depression 34 of the housing top 2c can be changed to come into contact with the circumferential edge portion of the packing 16 in a wall surface of an edge of the depression 34, thereby preventing the inclination of the packing 16.

Referring back to FIG. 1, the stator 14 and the packing 16 are provided with through-holes corresponding to the holes of the end portions of the flow channels 23, 25 arranged in the flow channel connection portion 4. The stator 14 and the packing 16 are fixed to the housing top 2c side by a stator fixing pin 20 in a state where these through-holes are positioned at the holes of the end portions of the flow channels 23, 25 of the housing top 2c. The housing top 2c is provided with a hole into which the stator fixing pin 20 is inserted, and the stator 14 and the packing 16 are provided with through-holes through which the stator fixing pin 20 penetrates the stator 14 and the packing 16, respectively.

The rotor 8 is rotated by the rotor drive shaft 6 inside the housing 2. The rotor drive shaft 6 is arranged perpendicular to the plane of the flow channel connection portion 4, and is provided with a rotor holding portion 6a at a forefront. A forefront surface of the rotor holding portion 6a is a plane parallel to the flow channel connection portion 4, and the rotor 8 is in contact with the stator 14 by being held by the forefront surface of the rotor holding portion 6a. A base end portion of the rotor drive shaft 6 is led outside the housing 2 through the hole 3 of the housing 2 to be rotated around a shaft center thereof by the rotor drive mechanism 100 including a rotation mechanism such as a motor and the like outside the housing 2. The rotor holding portion 6a and the rotor 8 are fixed by a rotor fixing pin 10 in a rotation direction, and the rotor 8 is rotated by the rotation of the rotor drive shaft 6. The rotor 8 is provided with a through-hole through which the rotor fixing pin 10 penetrates the rotor 8, and the rotor holding portion 6a is provided with a hole into which the rotor fixing pin 10 is inserted.

In the rotor drive shaft 6, the rotor holding portion 6a at the forefront portion has a larger outer diameter than that of a shaft portion on the base end side. A spring 7 in a compressed state is inserted between a bottom portion of the housing body 2a and the rotor holding portion 6a, and the rotor drive shaft 6 is biased to the housing top 2c side by the spring 7. This allows the rotor 8 to be pressed to the stator 14. In a surface on the stator 14 side of the rotor 8, a groove 12 is provided that forms a flow channel connecting flow channels of any one pair of the plurality of flow channels 23, of the housing top 2c, and a position of the groove 12 is changed by the rotation of the rotor 8.

When the rotor drive shaft 6 is rotated by the rotor drive mechanism 100, the position of the groove 12 is changed to switch the connection between the plurality of flow channels 23, 25 of the flow channel housing top 2c.

What is claimed is:

1. A flow channel switching valve, comprising:
a housing that has a plurality of connection ports connecting flow channel piping, and an internal space, and is provided with a flow channel connection portion as a plane projected from a periphery thereof, the flow channel connection portion being a region where holes of end portions of flow channels respectively leading to the connection ports are arranged in a flow channel connection plane, which is one plane of the internal space;
a stator that is contained inside the housing, is made of a flat plate-like member having a plane larger than the flow channel connection portion, and is fixed to a side of the flow channel connection plane of the housing;
a packing that is made of a flat plate-like member having a plane larger than the flow channel connection portion, and is sandwiched between the flow channel connection plane of the housing and the stator so that a central portion of one plane thereof tightly adheres to the flow channel connection portion;
a rotor that has a plane in contact with a plane of the stator on an opposing side of the packing inside the internal space of the housing, and is formed with a groove communicating between any one pair of the connection ports in the plane;
a rotor drive portion that rotates the rotor while sliding the rotor on the stator; and
a packing gland that is provided at a distance from the flow channel connection portion so as to surround an outer circumference of the flow channel connection portion in the flow channel connection plane of the housing, and is in contact with a circumferential edge portion of the packing on a same plane as the flow channel connection portion.

2. The flow channel switching valve according to claim 1, wherein in the packing gland, a member made of a material having a smaller modulus of elasticity than that of the packing is caused to tightly adhere to an inner wall of the housing.

3. The flow channel switching valve according to claim 2, wherein the packing is made of polyether ether ketone or polyimide, and the packing gland is made of polytetrafluoroethylene.

4. The flow channel switching valve according to claim 1, wherein the packing gland is made of a same material as that of the housing, and is formed integrally as a part of an inner wall of the housing.

* * * * *